US008019624B2

(12) United States Patent
Malone

(10) Patent No.: US 8,019,624 B2
(45) Date of Patent: Sep. 13, 2011

(54) ASSESSING ATHLETE INJURIES

(76) Inventor: K. Scott Malone, Warner Robins, GA (US)

(*) Notice: Subject to any disclaimer, the term of this patent is extended or adjusted under 35 U.S.C. 154(b) by 1368 days.

(21) Appl. No.: 11/371,864

(22) Filed: Mar. 9, 2006

(65) Prior Publication Data

US 2006/0206027 A1     Sep. 14, 2006

Related U.S. Application Data

(60) Provisional application No. 60/659,923, filed on Mar. 9, 2005.

(51) Int. Cl.
*G06Q 50/00* (2006.01)
(52) U.S. Cl. ............................................. 705/3; 705/2
(58) Field of Classification Search ............ 340/870.07; 600/300; 463/42; 705/2, 3
See application file for complete search history.

(56) References Cited

U.S. PATENT DOCUMENTS

| 6,515,593 | B1* | 2/2003 | Stark et al. ............... 340/870.07 |
| 2004/0019283 | A1* | 1/2004 | Lambert et al. ............... 600/476 |
| 2004/0241629 | A1* | 12/2004 | Ondrusz et al. ............... 434/247 |
| 2006/0183548 | A1* | 8/2006 | Morris et al. ................... 463/42 |
| 2006/0189852 | A1* | 8/2006 | Greenwald et al. ........... 600/300 |

* cited by examiner

*Primary Examiner* — Gerald J. O'Connor
*Assistant Examiner* — Teresa Woods
(74) *Attorney, Agent, or Firm* — Merchant & Gould

(57) ABSTRACT

Methods, systems, and computer program products assess injuries to elite athletes. A method involves receiving historical data associated with the athlete and receiving performance data from a functional assessment of the athlete. The functional assessment is designed based on a sport, a position, and/or the injury of the athlete. The method also involves querying a data source for mined data associated with athlete injuries similar to the injury being assessed, generating predictive data relevant to the injury, and analyzing the historical data, the performance data, the mined data, and/or the predictive data to produce a predictive analysis associated with the athlete.

20 Claims, 4 Drawing Sheets

ASSESSING ATHLETE INJURIES

RELATED APPLICATIONS

This utility patent application claims the benefit under 35 United States Code §119(e) of U.S. Provisional Patent Application No. 60/659,923 filed on Mar. 9, 2005, which is both hereby incorporated by reference.

COPYRIGHT NOTICE

A portion of the disclosure of this patent document contains material, which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

TECHNICAL FIELD

This invention relates to a method of assessing athlete injuries including an elite athlete injury assessment model.

BACKGROUND

A perplexing situation arises when clinically treating professional or elite athletes for injuries. Determining a fair way to assess these athletes for impairments and disability can be elusive. Conventional systems for assessing athlete injuries are based on the American Medical Association (AMA) guides to impairment and disability. These rules that govern impairments and disability for employee injuries, including the industrial working population, are state specific. After maximal medical improvement, if a permanent impairment is present, awards are based on the AMA guides to determine wage loss compensation.

Conventional methodologies for assessing athlete injuries leave much to be desired. For instance functional losses cannot be directly correlated with musculoskeletal impairment ratings. Further, evidence based research is lacking and there is limited data to support impairment percentages for the musculoskeletal system. Pain is usually a major complaint and is subjective. Still further, the system and methodology do not enable an examining physician to go beyond the AMA guides and incorporate adjustments for any functional loss. Thus, professional athlete injuries are analyzed using a standard system that applies to the industrial working population.

Accordingly there is an unaddressed need in the industry to address the aforementioned and other deficiencies and inadequacies.

SUMMARY

This Summary is provided to introduce a selection of concepts in a simplified form that are further described below in the Detailed Description. This Summary is not intended to identify key features or essential features of the claimed subject matter, nor is it to be used as an aid in determining the scope of the claimed subject matter.

Embodiments of the present invention include a process for assessing athlete injuries that is more indicative of conditioning and functional requirements associated with a specific sport, thus more objective in nature. The actual clinical evaluations are performed by experienced Sports Medicine Fellowship trained Professionals. Additionally, functional limitations are geared to sport and position specific injury models.

Embodiments of the present invention also include a new database developed for high-level or professional athletes. The main component of impairments should be based on objective lost functional abilities. Mining injury information on professional athletes generates the database. Similarly, predictive modeling and clinical examinations generate impairments. Thus, ultimate disability awards can incorporate the information from the elite athlete injury assessment (EAIA) model prior to finalizing compensation. This process may or may not incorporate with the AMA guides.

These and other features and advantages will be apparent from a reading of the following detailed description and a review of the associated drawings. It is to be understood that both the foregoing general description and the following detailed description are explanatory only and are not restrictive of the invention as claimed.

DETAILED DESCRIPTION

As briefly described above, embodiments of the present invention assess athlete injuries. In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents.

Figure 1:
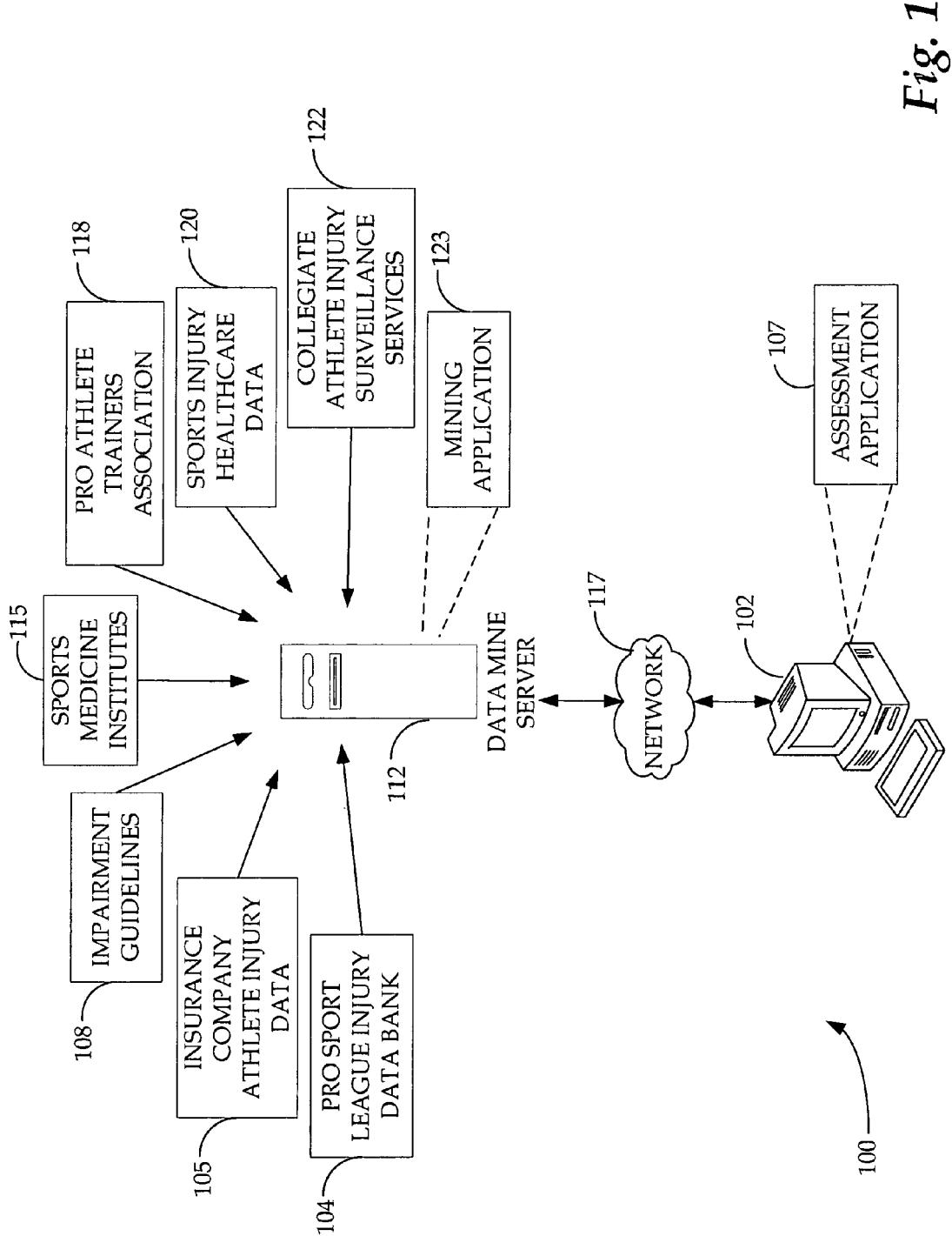
FIG. 1 is a block diagram illustrating aspects of a networked operating environment.

Referring now to the drawings, in which like numerals refer to like elements through the several figures, aspects of the present invention and an exemplary computing operating environment will be described. FIG. 1 and the following discussion are intended to provide a brief, general description of a suitable computing environment in which the invention may be implemented. While the invention will be described in the general context of program modules that execute in conjunction with an application program that runs on an operating system on a personal or server computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

Embodiments of the invention may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

DEFINITIONS

Injury—A wound or condition induced by accident or trauma. The injury arises out of and in the course of employment.

Impairment—is a loss of use or derangement of any body part, organ system, or organ function (AMA $5^{th}$ edition).

Medical Impairment—Can develop from an injury or illness.

Disability—is an alteration of an individual's capacity to meet personal, social, or occupational demands or statutory or regulatory requirements because of an impairment (AMA $5^{th}$ edition).

Functional loss—means a reduction in the ability of a body part or system to perform a task in its normal or usual way, compared with either known populations or the individual's prior known history.

Anatomical loss—means any measurable diminution of normal anatomic integrity, compared with either known populations or the individual's prior known history.

With regard to assessing injuries of elite athletes, key questions involve the following:

1. Causation—did the condition arise out of employment?
2. Impairment—is there an objective abnormality? Embodiments of the present invention include assessing anatomical and/or functional losses.
3. Disability—did the lessened capacity to carry out the job arise from the employment?
4. Legal issues—Does the assessment involve litigation? 14% of athlete injury assessments involve litigation.

FIG. 1 is a block diagram illustrating aspects of a networked operating environment 100. The operating environment 100 includes a computing apparatus 102 with an assessment application 107 residing therein. The computing apparatus 102 is in communication with a data mine server 112 via a network 117. The data mine server 112 includes a mining application 123 and athlete injury data from a variety of data sources. The data sources include professional sport league data banks 104, athlete injury data from insurance companies 105, impairment guide data 108, such as from an AMA guide, and sports medicine institutes 115. The data sources further include professional athlete trainer associations 118, sports injury data from healthcare institutions 120, and collegiate athlete injury surveillance services 122.

Examples of Key Parameters to be Included in Data Source Mine for a Population of Athletes

| Player Characteristics | Injuries | Career Status | Exposure |
|---|---|---|---|
| Athlete | Location | New Professional | Practice Settings |
| Sport | Mechanism | Collegiate | Game Settings |

-continued

| Player Characteristics | Injuries | Career Status | Exposure |
|---|---|---|---|
| Age | Contributing Factors | Established Professional | |
| Weight | Impairment | Retiring Professional | |
| Sex | | | |

The mining application 123 is a computational component operative to provide an objective evaluation of an elite athlete's physical condition and ability to perform his or her athletic specialty given physical condition, age, psychological status and any additional relevant personal circumstances. This evaluation will require access to pertinent historical data, acquired from credible sources. As briefly described above with respect to FIG. 1, these sources may be insurance providers, sports leagues, medical databases and other data collections compiled by organizations closely concerned with the performance, health, psychological state or statistical analysis of elite athletes' performance. As this pertinent data is acquired, it is compiled within a relational database management system (RDBMS), for example the data mine server 112, to facilitate the creation of data relationships and, more importantly, the application of sophisticated statistical analysis with an emphasis on predictive modeling. Additional details regarding the mining application 123 will be described below with respect to FIG. 3.

Figure 2:
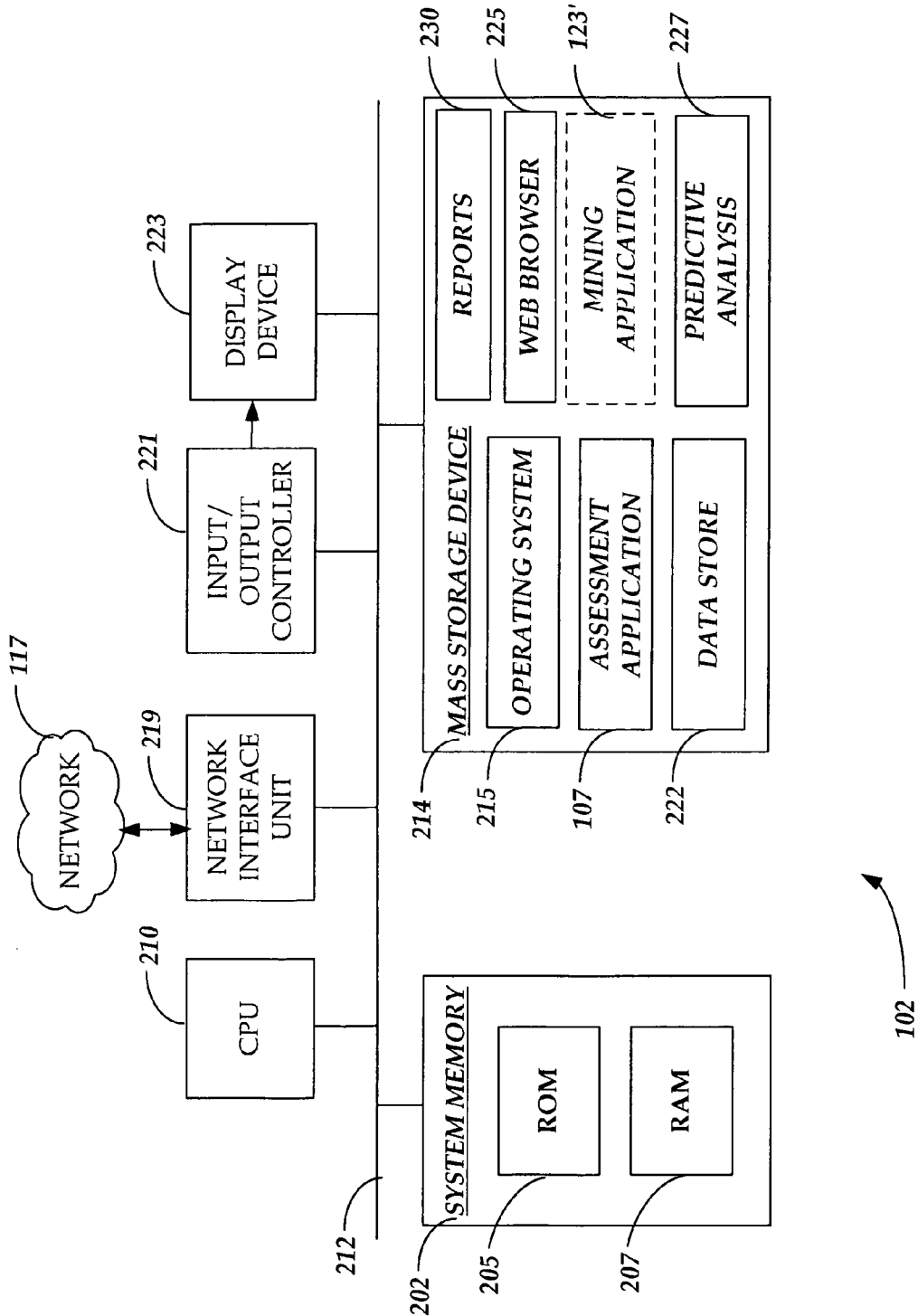
FIG. 2 illustrates computing system architecture for a computing apparatus.

FIG. 2 illustrates computing system architecture for the computing apparatus 102. In a basic configuration, the computing apparatus 102 typically includes at least one processing unit 210, system memory 202, and a mass storage device (MSD) 214. Depending on the exact configuration and type of computing apparatus 102, the system memory 202 may be volatile (such as RAM 205), non-volatile (such as ROM 207, flash memory, etc.) or some combination of the two. The MSD 214 typically includes an operating system 215 suitable for controlling the operation of a networked personal computer, such as the WINDOWS® operating systems from MICROSOFT CORPORATION of Redmond, Wash. The MSD 214 may also include one or more software applications such as the assessment application 107 and a web browser 225 such as INTERNET EXPLORER from MICROSOFT CORPORATION. It should be appreciated that in the alternative the mining application 123' may reside with the computing apparatus 102 instead of the data mine server 112.

The MSD 214 also includes a data store 222 for storing data received on the athlete being assessed, such as queried mined data, performance data, orthopedic data, and historical data, a predictive analysis 227 for use in generating reports 230 and making recommendations regarding the assessed injury. According to embodiments of the present invention, the applications are illustrative of any software application working in conjunction with the assessment application 107 and the mining application 123' to assess an injury to an athlete, such as an elite professional athlete. Dynamic Information from Insurance companies and injury data sources are downloaded or retrieved into the data mine server 112 and/or the computing apparatus 102.

Specific Information from the data mine server 112 is added to the "EAIA Computing Apparatus" 102 to begin development of the "Elite Athlete Injury Model" via the assessment application 107. Findings from independent reports are matched with key parameters from the Data Source Mine or data mine server 112 and the computing apparatus 102 and predictive injury statistics are generated based on percentiles and biostatistical measures. Additional details regarding the assessment application 107 will be described below with respect to FIG. 4.

The MSD 214 is connected to the CPU 110 through a mass storage controller (not shown) connected to the system bus 112. The MSD 114 and its associated computer-readable media, provide non-volatile storage for the computing apparatus 102. Although the description of computer-readable media contained herein refers to a MSD, such as a hard disk or RAID array, it should be appreciated by those skilled in the art that computer-readable media can be any available media that can be accessed by the CPU 210.

The CPU 210 may store data to and access data from the MSD 214. Data is transferred to and received from the MSD 214 through the system bus 212. The CPU 210 may be a general-purpose computer processor. Furthermore, as mentioned below, the CPU 210, in addition to being a general-purpose programmable processor, may be firmware, hardwired logic, analog circuitry, other special purpose circuitry, or any combination thereof.

According to various embodiments of the invention, the computing apparatus 102 can operate in a networked environment 100, as shown in FIG. 1, using logical connections to remote computing devices via network communication, such as an Intranet, or a local area network (LAN). The computing apparatus 102 may connect to the network 117 via a network interface unit 219. It should be appreciated that the network interface unit 219 may also be utilized to connect to other types of networks and remote computer systems. The computing apparatus 102 also includes an input/output controller 221 for receiving and processing input from a number of devices, including a keyboard (not shown). Similarly, the input/output controller 221 provides output to a display screen 223, a printer, or other type of output device.

A computing apparatus, such as the computing apparatus 102, typically includes at least some form of computer-readable media. Computer readable media can be any available media that can be accessed by the computing apparatus 102. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, disk drives, a collection of disk drives, flash memory, other memory technology or any other medium that can be used to store the desired information and that can be accessed by the computing apparatus 102.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 3:
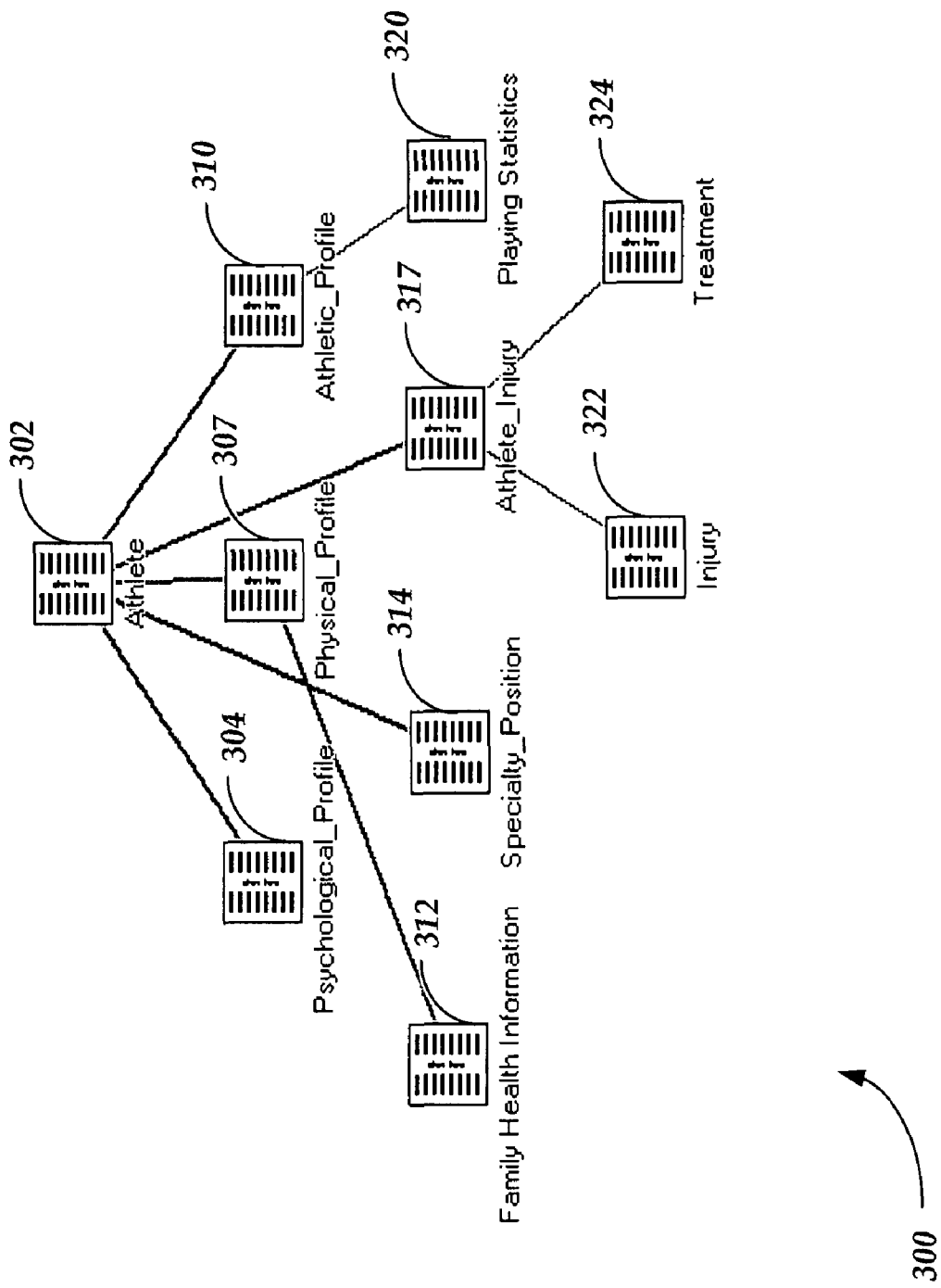
FIG. 3 illustrates data relationships utilized in producing valuable reporting.

FIG. 3 illustrates data relationships 300 utilized in producing valuable reporting. Using a sophisticated statistical analysis, a computational component, such as the mining application 123, produces objective reports that may be utilized by sports team owners, insurance companies, elite athletes, statisticians and anyone who has an interest in study populations of elite athletes based on the data relationships 300. The primary application of these reports will be to help determine functional limitations, impairments and/or disabilities. Likewise this process can help reveal probabilities for improvement and or degradation of performance levels at a specific point in an athlete's career.

In compiling a RDBMS, such as the data mine server 112, for the computational component, Sports Medicine Physicians and other Sports researchers work in tandem with experts in the art of computer programming to store pertinent data in an effective structure for analyzing the data populations used to produce the desired reporting and data maintenance. The RDBMS stores data pertinent to each athlete's specific sport, position, career and personal circumstances. Data variables are defined from within the collection of data, and mathematical constructs (for instance Chi-Square and Gamma statistical models) are applied in determining each variable's statistical significance in predicting data outcomes and making variable associations. For instance statistical analysis might be applied to determine how strongly a shoulder dislocation injury predicts that an outside linebacker's career will be shortened by 1-5 years.

The sample database below demonstrates how the computational component of the present application produces valuable elite athlete reporting. For the table definitions that follow, some column names provide the meaning of the data contained within them. Where necessary, a description is provided. For demonstration purposes a minimal amount of information is used:

Table Name: Athlete
Table Definition: A collection of each athlete's personal and health information.
Column 1: Athlete Code
   (Unique value an athlete.)
Column2: Athlete Name
Column3: Sport
Column4: Sport League
Column5: Specialty Code
   (Value representing an athlete's specialty or position within a sport.)
Column6: Career_Beginning_Date
Column7: Years_In_League
Column8: Career_Ending_Date
Column9: Age
Column10: Height
Column11: Weight
Column12: Team Code
   (Where applicable—Unique value representing the team with whom the athlete is employed.
Column13: Career_Status
("Active" or "retired")
Primary Key: Athlete Code
Table Name: Specialty Position
Table Definition: Information about a sports specialty or position within a sport.
Column1: Specialty Code
   (Unique value representing the specialty or position within a sport.)
Column2: Specialty_Position
   (Text name of sports specialty or position within a sport.)
Column3: Sport
Column4: League
Column5: Running_Speed_Weighting_Value
   (Numeric value gauging the role running speed plays in effective performance of the specialty or position.)

Primary Key: Specialty Code, League
Table Name: Injury
Table Definition: List of injuries suffered by athletes.
Column1: Injury_Code
  (Unique value representing an injury.)
Column2: Injury
  (Text name of the injury.)
Primary Key: Injury Code
Table Name: Treatment
Table Definition: List of treatment options for injuries.
Column1: Treatment Code
  (Unique value representing a type of treatment.)
Column2: Treatment
  (Text description of the treatment.)
Primary Key: Treatment Code
Table Name: Athlete Injury
Table Definition: List of each injury suffered by athletes.
Column 1: Athlete Code
  (Unique value an athlete.)
Column2: Injury Code
  (Unique value representing the injury suffered.)
Column3: Injury Sequence
  (Numeric value indicating sequence of injury occurrence throughout the athlete's career.)
Column2: Injury Date
  (Date which the injury occurred.)
Column3: Treatment Code
  (Unique value representing the treatment performed as a result of the injury.)
Primary Key: Athlete Code, Injury Code, Injury Sequence After these table structures have been created within an RDBMS, data analysis may begin using Structured Query Language (SQL). The following SQL programs demonstrate how the computational component of this patent may be implemented.

In order to find the average career length in years for running backs within the NFL who have played since 1980, the following program could be executed:

```
Select avg (Years_In_League)
From Athlete at1
Join Specialty Position sp1
On at1.Specialty_Code = sp1.Specialty_Code
Where at1.Career_Beginning_Date >= 1980 and
    at1.Sport = 'football' and
    at1.League = 'NFL' and
    sp1.Specialty_Positon = 'running back' and
    at1.Career_Status = 'retired'
```

To calculate the average number of years played after an NFL running back's first injury that required reconstructive knee repair—for athletes who have played since 1980, the following SQL program could be executed:

```
Select avg (date diff (year, Injury Date, Career_Ending_Date))
From Athlete at1
Join Specialty Position sp1
On at1.Specialty_Code = sp1.Specialty_Co
Join Athlete Injury ai1
On at1.Athlete_Code = ai1.Athlete_Code
Join (select Athlete Code,
         first_recon_surgery_seq = min (Injury Sequence)
      From Athlete Injury ai1
      Join Treatment tm1
      On ai1.Treatment_Code = tm1.Treatment_Code
      Where tm1.Treatment = 'reconstructive knee repair'
      Group by Athlete Code) ai2
On ai1.Athlete_Code = ai2.Athlete_Code and
   ai1.Injury_Sequence = ai2.Injury_Sequence
Where at1.Career_Beginning_Date >= 1980 and
    at1.Sport = 'football' and
    at1.League = 'NFL' and
    sp1.Specialty_Positon = 'running back' and
    at1.Career_Status = 'retired'
```

To calculate the percentage of NFL players since 1980, playing positions with "Running_Speed_Weighting_Value" greater than or equal to nine (the highest value is ten) who played more than five years after their first injury that required reconstructive knee repair and who had also suffered during their career at least one ACL tear requiring treatment, the following SQL program could be executed:

```
Select percentage_rbs = (is null (over_five, 0) / convert (float, count (distinct at1.Athlete_Code))) * 100
From Athlete at1
Join Specialty Position sp1
On at1.Specialty_Code = sp1.Specialty_Co
Join Athlete Injury ai1
On at1.Athlete_Code = ai1.Athlete_Code
Join (select Athlete Code,
         first_recon_surgery_seq = min (Injury Sequence)
      From Athlete Injury ai1
      Join Treatment tm1
      On ai1.Treatment_Code = tm1.Treatment_Code
      Where tm1.Treatment = 'reconstructive knee repair'
   Group by Athlete Code) ai2
On ai1.Athlete_Code = ai2.Athlete_Code and
   ai1.Injury_Sequence = ai2.Injury_Sequence
Join Athlete Injury ai3
On at1.Athlete_Code = ai3.Athlete_Code
Join Injury ij1
On ai3.Injury_Code = ij1.Injury_Code
Left outer join
      (Select at1.Athlete_Code,
          Over five = convert (float, count (distinct at1.Athlete_Code))
       From Athlete at1
       Join Specialty Position sp1
       On at1.Specialty_Code = sp1.Specialty_Co
       Join Athlete Injury ai1
       On at1.Athlete_Code = ai1.Athlete_Code
```

```
            Join (select Athlete Code,
                    first_recon_surgery_seq = min (Injury Sequence)
                From Athlete Injury ai1
                Join Treatment tm1
                On ai1.Treatment_Code = tm1.Treatment_Code
                Where tm1.Treatment = 'reconstructive knee repair'
                Group by Athlete Code) ai2
            On ai1.Athlete_Code = ai2.Athlete_Code and
                ai1.Injury_Sequence = ai2.Injury_Sequence
            Join Athlete Injury ai3
            On at1.Athlete_Code = ai3.Athlete_Code
            Join Injury ij1
            On ai3.Injury_Code = ij1.Injury_Code
            Where at1.Career_Beginning_Date >= 1980 and
                    at1.Sport = 'football' and
                    at1.League = 'NFL' and
                    sp1.Running_Speed_Weighting_Value >= 9 and
                    at1.Career_Status = 'retired' and
                    Date diff (year, ai1.Injury_Date, at1.Career_Ending_Date) >= 5 and
                    ij1.Injury = 'ACL tear') tt1
On at1.Athlete_Code = tt1.Athlete_Code
Where at1.Career_Beginning_Date >= 1980 and
        at1.Sport = 'football' and
        at1.League = 'NFL' and
        sp1.Running_Speed_Weighting_Value >= 9 and
        at1.Career_Status = 'retired' and
        ij1.Injury = 'ACL tear'
```

Using the sport-athlete-specialty specific approach of the computational component, more sophisticated data models are implemented to facilitate more complex analysis. Highly detailed profiles of each athlete are compiled. For instance an athlete's profile 302 might be divided into the subcategories of psychological 304, physical 307 and athletic 310. This way analysis may consider increasingly specific variables and how these variables affect an athlete's longevity in his specialty, his aptitude for recovery from injury and his ability to cope with life changes that may occur after his athletic career ends. For instance if a running back who incurs a possibly career ending leg injury, the following variables might be considered:

1) A detailed physical profile 307 is compiled the player's height, weight, body fat percentage, bone and connective tissue analysis, forty yard dash times as his career has progressed, bench press as his career has progressed, cardio pulmonary health, blood sugar levels, past usage or performance enhancing drugs, family health information 312, etc.

2) A playing or athletic profile 310 designed specifically for his athletic specialty 314 is compiled, his subcategory within the category of "running back"—tailback, halfback, etc., recording his playing style (power back, illusive, speed reliant runner, etc), playing style of teams that employed him (pass oriented, run oriented), playing statistics 320 such as the player's number of run attempts per season, the number of games he played on artificial surfaces, the number of times he was forced to leave games because of injury 322 (some will of course not require medical treatment 324) or poor performance, athlete injuries 317 such as number of concussions throughout his career, and all of his performance statistics 320, etc.

3) A psychological profile 304 is performed on the player, gathering his basic outlook on life, his educational level, his family status, his friend and family support structure, the degree to which he is optimistic or pessimistic, his self discipline, his track record in past physical therapy regimens, his past relationships with players and coaches, past drug dependencies, etc.

After the creation of an effectively designed RDBMS, the computational component requires the design and implementation of programs much like the previous SQL examples. These programs mine elite athlete data to produce valuable reporting for sports team owners, insurance companies, statisticians and anyone interested in the statistical data produced. These reports facilitate an objective assessment of an athlete's career at any juncture, allowing all concerned parties to make informed decisions about an athlete's career direction, especially during contract negotiations following injury. Additionally, this computational tool provides athletes with information that will help them act proactively, financially, and educationally before and after injury in preparing for a life and career outside of athletics. Additional details regarding report generated from the queried data will be described below with respect to FIG. 4.

Figure 4:
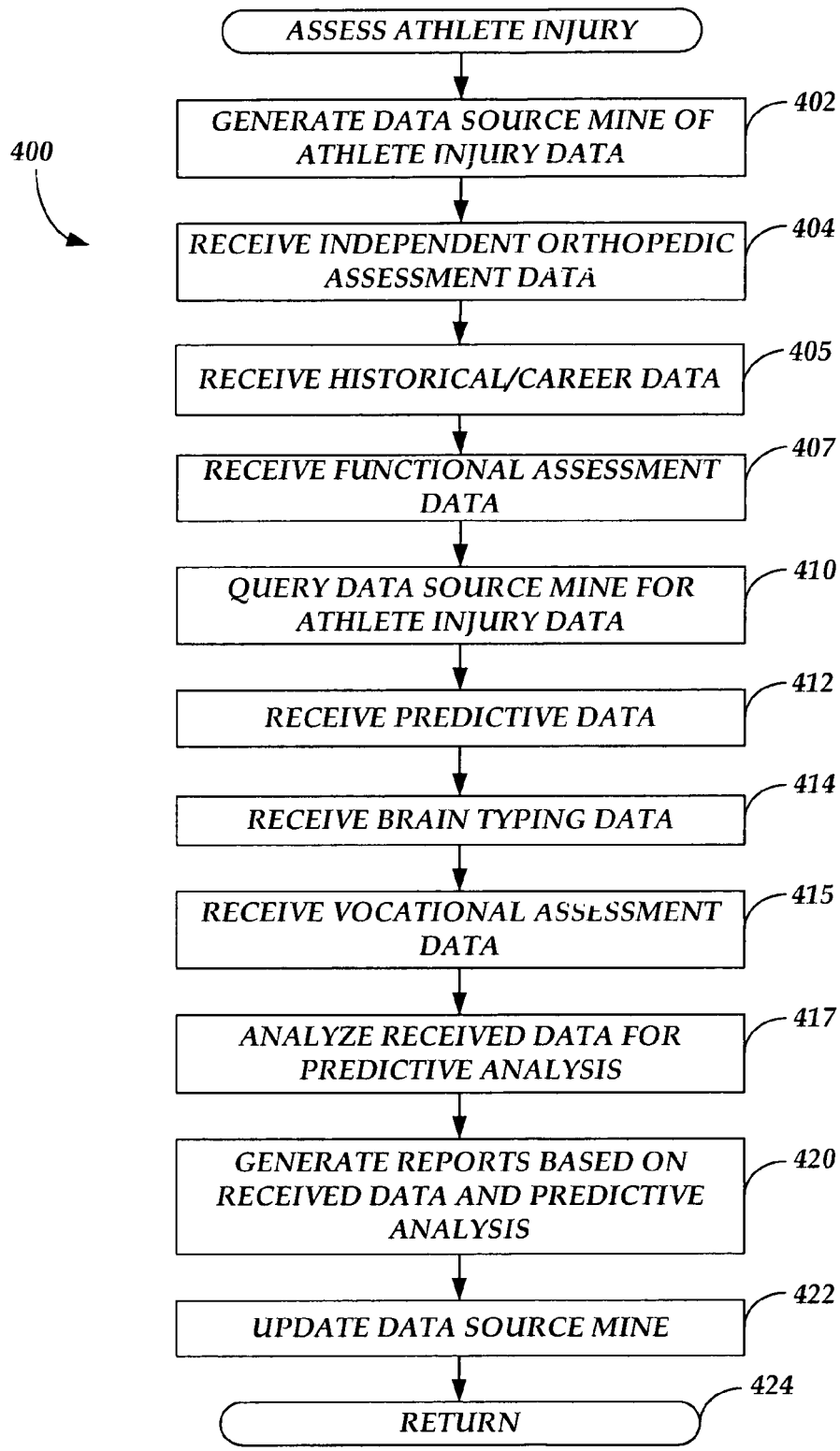
FIG. 4 illustrates a logical or operational flow performed in assessing athlete injuries.

FIG. 4 illustrates a logical or operational flow 400 performed in assessing athlete injuries according to an embodiment of the present invention. When reading the discussion of the routines presented herein, it should be appreciated that the logical operations of various embodiments of the present invention are implemented (1) as a sequence of computer implemented acts or program modules running on a computing system and/or (2) as interconnected machine logic circuits or circuit modules within the computing system. The implementation is a matter of choice dependent on the performance requirements of the computing system implementing the invention. Accordingly, the logical operations illustrated in FIG. 4, and making up the embodiments of the present invention described herein are referred to variously as operations, structural devices, acts or modules. It will be recognized by one skilled in the art that these operations, structural devices, acts and modules may be implemented in software, in firmware, in special purpose digital logic, and any combination thereof without deviating from the spirit and scope of the present invention as recited within the claims set forth herein.

Referring now to FIGS. 1-4, the logical flow 400 begins at operation 402, where the data mine server 112 generates a data source mine of athlete injury data. Here the data mine server 112 receives athlete injury data from one or more sources, such as insurance companies 105 and professional sports injury data banks 104. The data mine server 112 then organizes the athlete injury data for accessibility to produce the mined data based on sports, positions, physiology of the athletes, career status, exposure of the athletes, and/or injuries associated with the athlete injury data of athletes and stores the mined data in the data source. Next, an independent orthopedic assessment is conducted and the computing apparatus 102 receives the independent orthopedic assessment data at operation 404. Additional details regarding this orthopedic assessment is described below with regard to Scenarios A-C.

At operation 405, the computing apparatus receives historical and career data on the athlete being assessed. This may include receiving pre-existing medical conditions and a current career status of the athlete. The current career status includes information associated with a start of a career of the athlete, an injury during the career, or an end of the career.

Next, a functional assessment is designed based on the injury, sport, and/or position of the athlete being assessed. The functional assessment is then conducted and at operation 407, the computing apparatus 102 receives functional assessment data. At operation 410, the computing apparatus 102 queries the data source, for example the data mine server 112, for mined data associated with injuries similar to the injury being assessed. The logical flow 400 then continues to operation 412.

At operation 412, the computing apparatus 102 receives the mined data as predictive data relevant to the injury. The computing apparatus 102 uses the mined data to make predictions about the assessed injury. Next, at operation 414, the computing apparatus 102 receives data associated with a brain typing evaluation of the athlete and at operation 415 receives vocational data associated with a vocational assessment of the athlete. The logical flow 400 then continues to operation 417.

At operation 417, the computing apparatus 102 analyzes the received data to produce a predictive analysis associated with the athlete being assessed. The received data analyzed includes the historical data, the performance data, the mined data, the orthopedic data and/or the predictive data. Then at operation 420, the computing apparatus generates reports based on the received data and the predictive analysis. The reports may include the predictive analysis and recommendations based on the predictive analysis.

Generating a report may include calculating impairment of the athlete at least in part due to the injury, predictive injury statistics based on percentiles and biostatistical measures, probability of the injury reoccurring, and marketability of the athlete based on the injury. Other reports may include the independent orthopedic assessment, the functional assessment including impairment, the predictive data relevant to the injury, the brain typing evaluation, and the vocational assessment. Additional details regarding reports and queries will be described below with respect to Scenarios A-C.

Next, at operation 422, the computing apparatus 102 updates the data source with data associated with the predictive analysis associated with the athlete assessed. Thus, the computing apparatus 102 adds more data to the athlete injury data store in the data mine server 112 after each assessment. The logical flow 400 then returns control to other routines at return operation 424.

The predictive analysis is a valuable to that can be used in association with the following: athlete contract negotiations, workmens compensation decisions, functional performance baselines due to a new injury, and pre-existing injury assessments prior to athlete participation with a new team. The predictive analysis may also be used for career ending injury settlements, athlete retirement settlements for injuries obtained during career, injury treatment recommendations, and expert opinions in court.

The EAIA model involves gathering medical history and information associated with an athlete to be assessed, arranging for and conducting independent orthopedic and functional evaluation at key locations, and providing those orthopedic and functional tests based on the position, sport, and/or injury of the athlete. The following Scenarios A-C illustrate both hypothetical functional and orthopedic assessment reports and predictive queries:

SCENARIOS

Scenario A - JOHN DOE

I. EAIA Model Report

Performed at Houston Orthopedic Surgery and Sports Medicine It is the goal of this examination and assessment to provide more objective data than the traditional pre-draft process. The independent orthopedic examination was provided by a Fellowship Trained Sports Medicine. Orthopedist. The sports specific and injury specific functional testing was designed and performed by a Licensed/Certified Athletic Trainer or Licensed

| | |
|---:|:---|
| Client: | John Doe |
| SSN: | 111-22-333 |
| DOB: | 5-25-1985 |
| DOI: | 11/2003 |
| Position: | Offensive Lineman |
| Diagnosis: | Status-Post Right Knee ACL Reconstruction |
| Claim #: | 55558888 |
| Work Status: | Preparing for NFL Draft |

Physical Therapist.

Referred By: Never Lose Professional Football Team

Thank you for referring Mr. John Doe for an evaluation and testing. His test was performed on 1/24-25/2004 from 1 pm to 4 pm both days. Mr. Doe was very motivated during performance of testing.

A. Medical History

John Doe is a twenty one year old collegiate offensive lineman, who is planning to enter the National Football League. He was a collegiate All American for two years, but unfortunately he injured his right knee in November of 2003 prior to completing his senior year.

He was diagnosed with an Anterior Cruciate Ligament Tear (ACL) and a Medial Collateral Ligament Tear (MCL). His treatment consisted of bracing for four weeks to allow healing of MCL. He then proceeded to have ACL reconstructive surgery. He has worked hard in his rehabilitation program and progressed well. John has now been cleared for full contact participation by his team physician.

John Doe's medical records indicate no previous history of significant injury. His operation notes indicate he had a complete tear of the ACL and a Grade III MCL injury. An ACL bone patella tendon allograft repair was performed in December 2003.

He participated in six months of traditional rehabilitation and his medical records indicate he was very compliant. He has been lifting and running without any complications, however he has not participated in contact since his injury in 2003.

He was referred for an independent orthopedic examination. Also, a sports and injury specific functional assessment was requested by the Never Lose Professional Football Team.

I.

Sport and Injury Specific Test Results

| B. | Demonstrated Ability | Page Ref. |
|---|---|---|
| Strength | | |
| Biodex | | |
| Extension | 96% of uninvolved side | |
| Flexion | 98% of uninvolved side | |
| Functional Gait Test | | |
| Jogging | No Abnormalities Observed | |
| Running | No Abnormalities Observed | |
| Sprinting | No Abnormalities Observed | |
| Single Rep. Max. Squat | 850 lbs. | |
| Single Rep. Max Bench | 375 lbs. | |
| NFL Combine Simulation | | |
| Vertical Jump | 24 inches | |
| Single Leg Jump - involved | 18 inches | |
| Single Leg Jump - uninvolved | 19 inches | |
| Drop Jump | 21 inches | |
| Standing Broad Jump | 8 feet | |
| Squat Jump | 29 inches | |
| Counter Movement Jump | 22 inches | |
| Shuttle Jump Tests | | |
| Involved Side | 40 | |
| Uninvolved Side | 45 | |
| Agility Tests | | |
| Shuttle Run | | |
| Timed Agility Test (505) | 16.3 seconds | |
| Ergo meter Sprint Test | | |
| Ergo meter Fatigue Test | | |
| 10-yard Sprint Test | 4.2 seconds. | |
| 20-yard Sprint Test | 5.3 seconds. | |
| 40-yard Sprint Test | 8.6 seconds. | |

I.

C. Summary of Key Findings

Mr. John Doe demonstrated normal gait patterns while performing all tests. No obvious signs of distress were noted during performance of exercises over 2 day period. His demonstrated abilities matched well with the position demands of a NFL Offensive Lineman.

Key Comments:

A) Knee stability excellent per Independent Orthopedic Exam.
        1. Good Quadriceps Girth
        2. Negative Pivot Shift
        3. Negative Lachmans
        4. No Swelling B) Functional Sports Specific Testing
        1. Vertical Jump
        2. 10 yard Sprint
        3. 20 yard Sprint
        4. Timed Agility Test

II. Independent Orthopedic Evaluation

Examiner:

J.A. Drews M.D.

See Attached Report

III. Recommendations

Mr. Doe's knee range of motion was normal for the involved knee. There was no significant anterior laxity when comparing involved knee to uninvolved knee. Gait patterns are normal in visual based comparisons.

Mr. Doe will benefit from a continued weight lifting program and agility program for strength and speed, which will allow him to maintain the essential skills required for a professional football offensive lineman.

IV. Predictions & Predictive Modeling Sample Questions

To be queried by the EAIA Computing Apparatus a) What are the chances of re injury?

b) What are the percentages of injuries to the opposite side?

c) What is the average career in years of a NFL offensive line?

d) What types of injuries are most common to offensive linemen?

e) What is the average injury claim cost of NFL offensive lineman?

f) What is the average injury settlement cost due to medical retirement and retirement at the end of a career?

g) What is normative data for aerobic fitness, speed tests, body composition, and strength for NFL offensive linemen?

H) What is normative data for NFL combine tests – broad jump, vertical jump, short shuttle, long shuttle, three-cone drill, and forty yard dash for offensive linemen.

ORTHOPEDIC EVALUATION
SCENARIO A

| | |
|---|---|
| Player's Name: | John Doe |
| DOB: | 5-25-1985 |
| SSN: | 111-22-3333 |
| Date: | 1-15-2004 |

| | |
|---|---|
| Date of Examination | 1-11-2004 |
| Sports Medicine Physician: | J.A. Drews, M.D. |
| Identification:<br>collegiate<br>considered by | The patient is a twenty-one year old male offensive lineman who is being<br><br>Never Lose Professional Football team for potential draft pick in March NFL Draft. |
| Current Complaints: | The patient is a healthy, 298 lbs. male who injured his right anterior cruciate and medial collateral ligaments in November 2003. He had an anterior cruciate ligament reconstruction in 12-2003. He currently reports he is free of acute injury and he has completed rehabilitation. He is Currently lifting and running under his own Supervision. |

Past Medical History:

1. He has had right anterior cruciate ligament (ACL) reconstruction performed in December 2003. He has no current symptoms of instability, swelling, or locking. No previous significant injuries noted in records provided at the time of testing.

| | | |
|---|---|---|
| Medications: | Aleve – as needed. | |
| Hospitalization: | December 2003 – ACL reconstruction. | |

Physical Examination:

| | | |
|---|---|---|
| Vital Signs: | Height: | 78 inches |
| | Weight: | 298 lbs. |
| | Blood Pressure: | 123/82 |
| | Pulse: | 80 beat per minute |
| | Respirations: | 20 pm |

Cervical Spine: The patient's cervical spine is well aligned. He flexes to Point of touching his chin on his chest. He can extend fully. Rotation is present bilaterally to 80 degrees. Spurling's test is negative. No adenopathy is present. He had good cervical pulses.

Thoracic/Lumbar Spine: There is no evidence of scoliosis or lordosis. He has no

No limitation to flexion, extension, or lateral bending. He has no pain on motion. Straight Leg Raise (SLR) is negative. He has equal leg lengths. No atrophy of musculature in the lower extremity.

Neck: He is not complaining of any radiating pain from his Neck. The range of motion (ROM) of the neck is normal. There is no occipital, paracervical, or trapezius tenderness to palpation. The reflexes, sensation, and muscle tone are normal.

Shoulders:
Left: He reports no pain with shoulder motion. He has no atrophy of shoulder muscles. He can forward flex and abduct his left shoulder to 180 degrees of motion and extend to 30 degrees. He can bring his left thumb to the level of T9 of his thoracic spine, suggesting excellent internal rotation and it is present at 40 degrees. He can externally rotate left shoulder to 95 degrees. He has

| | |
|---|---|
| Right: | negative apprehension sign. Impingement test is negative. He has no pain with rotation of shoulder. He reports no pain with shoulder motion. He has no atrophy of shoulder muscles. He can forward flex and abduct his right shoulder to 180 degrees of motion and extend to 30 degrees. |
| | He can bring his right thumb to the level of T9 of his thoracic spine, suggesting excellent internal rotation and it is present at 40 degrees. He can externally rotate right shoulder to 95 degrees. He has negative apprehension sign. Impingement test is negative. He has no pain with rotation of shoulder. |
| Wrist/Hands: | He flexes and extends his fingers without pain or Difficulty. His wrists flex and extend well. Grip strength is 160 lbs. on the right and 154 lbs. on the left. Pinch strength is 30 lbs. on the right and 29 lbs. on the left. This indicates no significant difference in grip strength in a right handed player. |
| Hips/Pelvis: | The hips and pelvis show that the pelvis is non-tender With palpation. His hips rotate fully and there is no indication flexion and extension. |
| Knees: | There is no effusion in either knee at the present time. |
| Left: | His left knee non-tender to palpation. His knee flexes to 130 degrees and extends to 0 degrees. He has no medial or lateral instability in 30 degrees of flexion. He has a negative flexion pinch test on both the medial and lateral menisci. His anterior cruciate shows an excellent end point. He has no pivot shifting. |
| Right: | His right knee shows a well-healed anterior incision from The superior pole of the patella to the tibia tubercle along the medial aspect of his patella tendon. He has three portal incisions that are closed and well healed. He demonstrates 130 degrees flexion of the right knee and 0 degrees extension of his knee. He has no medial or lateral instability at 30 degrees of flexion. He has a solid end point with Lachman's and Anterior Drawer Tests. |

|  |  |
|---|---|
|  | He has no patellofemoral crepitus or patella instability. McMurry's Test was negative. He has good quadriceps strength as well as hamstring strength. He has an essentially normal right knee examination. |
|  | *Notes*: It is noted that we did a KT-2000. The anterior translation on right was 1 mm more than the left in bilateral comparison. |
| Ankles/Feet: Left: | The left foot is currently not bothering him. He reports a history of ankle sprains which were treated by medical staff at college. Standing alignment is normal with plantar flexion, dorsiflexion, inversion, and eversion ROMs within normal limits. |
| Right: | The right foot is currently not bothering him. He reports a history of ankle sprains which were treated by medical staff at college. Standing alignment is normal with plantar flexion, dorsiflexion, inversion, and eversion ROMs within normal limits. |
| Cardiac Examination: minute with no | The patient has a regular sinus rhythm of 80 beats per Murmurs, clicks, or other abnormalities detected. |
| Pulmonary Examination: | The patient has clear lung fields bilaterally to auscultation and percussion. |
| Abdominal Examination: | The patient has a mild protuberant abdomen which is soft and non-tender. There is no hepatosplenomegaly palpable. |
| Vascular Examination: | The patient has bounding upper and lower extremity pulses at all sights with no evidence of impaired arterial or venous function. |

Impression: Status post right anterior cruciate reconstruction, 2003 with successful results and no symptoms at this time. An excellent KT-2000 demonstration of stability.

Scenario B - -DON DOE

I. EAIA Model Report

Performed at Houston Orthopedic Surgery and Sports Medicine

It is the goal of this examination and assessments to provide more objective

| | |
|---:|---|
| Client: | Don Doe |
| SSN: | 222-22-333 |
| DOB: | 4-25-1979 |
| DOI: | 07/2002 |
| Position: | Pitcher |
| Diagnosis: | Status-Post Rt. Shoulder Rotator Cuff Repair |
| Claim #: | 1234568 |
| Work Status: | Not Currently Working | data than the traditional pre-draft process. The independent orthopedic examination was provided by a Fellowship Trained Sports Medicine Orthopedists. The sports specific and injury specific functional testing was designed and performed by a Licensed/Certified Athletic Trainer or Licensed Physical Therapist.

Referred By:

Thank you for referring Mr. Don Doe for an evaluation and testing. His test was performed on 10/4-5/2003 from 1 pm to 4 pm both days. Mr. Doe was very motivated during performance of testing.

A. Medical History

Don Doe is a 27 year old right hand pitcher for John Q Professional Baseball Team. He injured his Right Shoulder in the July of 2002 pitching into the eighth inning. He was diagnosed with a Rotator Cuff Tear. He was treated conservatively with rehabilitation program consistent with strengthening of the Rotator Cuff Complex. He continued to report discomfort and MRI results revealed an undersurface Rotator Cuff tear.

Don Doe's medical records indicate previous history of right Elbow MCL sprain which was treated conservatively in Triple A baseball league. Records indicate full recovery and progression back into pitching rotation. His pre-injury pitching speed indicates capabilities of 90 to 90+ mph.

Don Doe under went an arthroscopic sub-acromial decompression and repair of his Rotator Cuff with 1 anchor in November 2002. He has completed rehabilitation and he has been cleared for full participation by his surgeon. He has been lifting and throwing without any complications. He has not thrown full speed in a game to this date.

Don Doe has been referred for independent orthopedic examination and sport specific/injury specific functional assessment for objective data to determine his return to competitive pitching in relation to injury by Joe Q Professional Baseball Team.

I.

Sport and Injury Specific Test Results

| B. | Demonstrated Ability | Page Ref. |
|---|---|---|
| Strength | | |
| | | |
| Internal Rotation | 92% of uninvolved side | |
| External Rotation | 90% of uninvolved side | |
| Functional Test | | |
| Pitch Speed | 80 mph | |
| Seated Bench Press Throw (6lbs. ball) | 20 ft. 5 inches | |
| Single Bench Press Max. | 250 lbs. | |
| Dips to Fatigue | 20 reps. | |
| Diagonal Pulley Test | 30 lbs. | |
| Ergometry | | |
| UBE 30 rpms sprint | 4.5 minutes | |
| 60 rpms sprint | 3.75 minutes | |
| 90 rpms sprint | 2.5 minutes | |
| | | |
| | | |
| | | |
| | | |
| | | |
| Sprint Test | | |
| | | |
| | | |
| | | |
| | | |
| 20-yard Sprint Test | 5.3 seconds. | |
| 40-yard Sprint Test | 8.6 seconds. | |

C. Summary of Key Findings

*Key Comments:*     A) The main functional limitations are decreased internal range of motion and some weakness in the rotator cuff complex.

B) He had no complaints of pain.

III. Independent Orthopedic Evaluation

Examiner: J.A. Drews – Report attached.

III. Recommendations

Don Doe's functional testing revealed reasonable results. He still needs to work on restoring his velocity. It is not uncommon after surgery for a professional pitcher to have decreased velocity.

I would recommend a biomechanical analysis of his throwing motion. If he had a pre-injury video analysis, there shoulder be a comparison.

It is our opinion he is capable of returning to a pitching rotation.

I would recommend he start with limited innings or be used as a closer. I would monitor his pitch count closely.

He will need to continue to work on strengthening his rotator cuff and scapular stabilizer complex.

I would repeat functional testing of his rotator complex quarterly.

IV. Predictions/Predictive Modeling Sample Questions

To be queried by the EAIA Computing Apparatus a) What are the chances of re injury?

b) What is the average career for a professional pitcher with this type of injury?

c) What types of injuries are most common to professional baseball pictures?

d) Is there a relationship of rotator cuff injuries with starting versus closing professional pictures?

e) Average injury settlement cost due to medical retirement and retirement at the end of a career.

f) What is normative data for aerobic fitness, speed tests, body composition, and strength for professional baseball pitchers?

g) Is there a correlation with rotator cuff injuries and the age of the professional baseball pitchers?

ORTHOPEDIC EVALUATION

| | |
|---|---|
| Player's Name: | Don Doe |
| DOB: | 4-25-1979 |
| SSN: | 222-22-333 |
| Date: | 10-11-2003 |

| | |
|---|---|
| Date of Examination | 10-1-2003 |
| Attending Physician: | J.A. Drews, M.D. |
| Identification: | The patient is a twenty-seven year old male professional baseball player pitcher who is being considered by John Q Professional Baseball team for return to a starting rotation. He has only been able to be used as a reliever. |
| Current Complaints: | Mr. Don Doe has had chronic shoulder pain for over three years. A Medical work up including a MRI arthrogram revealed he had a partial rotator cuff tear. He currently Reports he is free of acute injury and he has Completed regimen of physical therapy. He is Currently lifting and throwing under his pitching |
| coaches | |
| | Supervision. He has not thrown full speed in |
| game to date. | |

Past Medical History:

2. He had right rotator cuff repair and subacromial decompression performed in November 2002. He has no current symptoms of instability, swelling, or locking. Previous significant injuries noted in records provided at the time of testing were Medial Collateral Ligament Sprain of his right elbow. The injury was treated conservatively with full recovery.

| | |
|---|---|
| <u>Medications:</u> | OTC – Aleve – as needed. |

Hospitalization: November 2002

Physical Examination:

| | | |
|---|---|---|
| Vital Signs: | Height: | 76 inches |
| | Weight: | 218 lbs. |
| | Blood Pressure: | 123/82 |
| | Pulse: | 80 bpm |
| | Respirations: | 20 pm |

Cervical Spine: The patient's cervical spine is well aligned. He flexes to point of touching his chin on his chest. He can extend fully. Rotation is present bilaterally to 80 degrees. Spurling's test is negative. No adenopathy is present. He had good cervical pulses.

Thoracic/Lumbar Spine: There is no evidence of scoliosis or lordosis. He has no

No limitation to flexion, extension, or lateral bending. He has no pain on motion. Straight Leg Raise (SLR) is negative. He has equal leg lengths. No atrophy of musculature in the lower extremity.

Neck: He is not complaining of any radiating pain from his neck. The range of motion (ROM) of the neck is normal. There is no occipital, paracervical, or trapezius tenderness to palpation. The reflexes, sensation, and muscle tone are normal.

Shoulders:
    Left: He reports no pain with shoulder motion. He has no atrophy of shoulder muscles. Non-tender to palpation of the acromioclavicular joint or anteriorly over the long head of the Biceps Tendon. He can forward flex and abduct his left shoulder to 180 degrees of motion and extend to 30 degrees.

|  |  |
|---|---|
|  | He can bring his left thumb to the level of T9 of his thoracic spine, suggesting excellent internal rotation. He can bring his thumb to the level of C7 of his cervical spine, suggesting good external rotation. He can externally rotate left shoulder to 95 degrees. He has negative apprehension sign. Impingement test is negative. He has no pain with rotation of shoulder. |
| Right: | He reports no pain with shoulder motion. He has no atrophy of shoulder muscles. Non-tender to palpation of the acromioclavicular joint or anteriorly over the long head of the Biceps Tendon. His arthroscopic portal incisions are closed and well healed. He can forward flex his right shoulder to 180 degrees of motion, abduct his shoulder with external rotation to 180 degrees and extend to 30 degrees. |
|  | He can bring his right thumb to the level of T11 of his thoracic spine, suggesting slight decrease in internal rotation. He can bring his thumb to the level of T3 of his Thoracic spine, suggesting excellent external rotation. He can externally rotate right shoulder at 90 degrees abduction to 150 degrees and internally rotate to 75 degrees. He has negative apprehension sign. Impingement test is negative. He has no pain with rotation of shoulder. Negative Speeds Test. Negative O'Brien's Test. No pain with Gerber Lift Off. |
| Elbows: | There is no effusion in either elbow at the present time. Visually, musculature is equal and symmetrical. His extension range of motion is 0 degrees bilaterally and his flexion range of motion is 160 degrees bilaterally. Valgus stress tests were negative in bilateral comparison. Varus stress tests were negative in bilateral comparison. |

| | |
|---|---|
| Wrist/Hands: | He flexes and extends his fingers without pain or difficulty. His wrists flex and extend well. Grip strength is 160 lbs. on the right and 154 lbs. on the left. Pinch strength is 30 lbs. on the right and 29 lbs. on the left. This indicates no significant difference in grip strength in a right handed player. |
| Hips/Pelvis: | The hips and pelvis show that the pelvis is non-tender with palpation. His hips rotate fully and there is no indication flexion and extension. |
| Knees: | There is no effusion in either knee at the present time. |
| Left: | His knee is non-tender to palpation. His knee flexes to 130 degrees and extends to 0 degrees. He has no medial or lateral instability in 30 degrees of flexion. He has a negative flexion pinch test on both the medial and lateral menisci. His anterior cruciate shows an excellent end point. He has no pivot shifting. |
| Right: | His knee is non-tender to palpation. His knee flexes to 130 degrees and extends to 0 degrees. He has no medial or lateral instability in 30 degrees of flexion. He has a negative flexion pinch test on both the medial and lateral menisci. His anterior cruciate shows an excellent end point. He has no pivot shifting. |
| Ankles/Feet: | |
| Left: | Standing alignment is normal with plantar flexion, dorsiflexion, inversion, and eversion ROMs within normal limits. Stability testing is normal and without pain. |
| Right: | Standing alignment is normal with plantar flexion, dorsiflexion, inversion, and eversion ROMs within normal limits. Stability testing is normal and without pain. |

| | |
|---|---|
| Cardiac Examination: | The patient has a regular sinus rhythm of 80 bpm with no murmurs, clicks, or other abnormalities detected. |
| Pulmonary Examination: | The patient has clear lung fields bilaterally to auscultation and percussion. |
| Abdominal Examination: | The patient has a mild protuberant abdomen which is soft and non-tender. There is no hepatosplenomegaly palpable. |
| Vascular Examination: | The patient has bounding upper and lower extremity pulses at all sights with no evidence of impaired arterial or venous function. |
| Impression: | Status-post arthroscopic rotator cuff repair and subacromial decompression with normal recovery. |

Scenario C-RON DOE

I. EAIA Model Report

Performed at Houston Orthopedic Surgery and Sports Medicine

It is the goal of this examination and assessments to provide more objective data than the traditional pre-draft process. The independent orthopedic Examination was provided by a Fellowship Trained Sports Medicine Orthopedist. The sports specific and injury specific functional testing was designed and performed by a Licensed/Certified Athletic Trainer or Licensed Physical Therapist.

| | |
|---:|---|
| Client: | Ron Doe |
| SSN: | 221-21-3331 |
| DOB: | 11-25-1968 |
| DOI: | 07/2002 |
| Position: | Offensive Lineman |
| Diagnosis: | Lumbar Disk Rupture and Status-Post Bilateral Shoulder Rotator Cuff Partial Repair |
| Claim #: | 980656 |
| Work Status: | Not Currently Working |

Referred By: John Q. Professional Football Team

Thank you for referring Mr. Ron Doe for an evaluation and testing. His test was performed on 3/4-5/2005 from 1 pm to 4 pm both days. Mr. Doe was very motivated during performance of testing.

A. Medical History

Ron Doe is a 37 year old, 305 lbs. male that is a 17 year veteran NFL Offensive Lineman. He has a recent history of a Lumbar Disc Rupture. He has had bilateral shoulder surgery for Rotator Cuff tears. Mr. Doe also has a history of right Knee surgery for ACL and medial Meniscus tears. He has a history of left Knee arthroscopic surgeries for medial and lateral meniscus tears. Records indicate a history of Ankle and Elbow sprains treated by medical staff with full recovery.

He is contemplating retirement, but he may return if medically cleared by physicians.

Mr. Doe is referred for independent orthopedic evaluation and sport specific position specific functional assessment.

I.

Sport and Injury Specific Test Results

| B. | Demonstrated Ability | Page Ref. |
|---|---|---|
| Strength | | |
| | | |
| Internal Rotation | 92% of uninvolved side | |
| External Rotation | 90% of uninvolved side | |
| Functional Test | | |
| | 80 mph | |
| Seated Bench Press Throw (6lbs. ball) | 20 ft. 5 inches | |
| Single Bench Press Max. | 350 lbs. | |
| Dips to Fatigue | 20 reps. | |
| Diagonal Pulley Test | 30 lbs. | |
| Ergometry | | |
| UBE 30 rpms sprint | 4.5 minutes | |
| 60 rpms sprint | 3.75 minutes | |
| 90 rpms sprint | 2.5 minutes | |
| | | |
| | | |
| | | |
| | | |
| | | |
| | | |
| | | |
| Sprint Test | | |
| | | |
| | | |
| | | |
| | | |
| | | |
| 20-yard Sprint Test | 5.3 seconds. | |
| 40-yard Sprint Test | 8.6 seconds. | |

C. Summary of Key Findings

Key Comments:

Bilateral Shoulder stability excellent per Independent Orthopedic Exam.

5. Good ROM and Strength
    6. Negative Shift Anterior/Posterior Bilaterally
    7. Negative Sulcus Sign
    8. No Swelling, discoloration, or deformities B) Lumbar Disk Rupture stability per Independent Orthopedic Exam.

1. Good ROM and Strength
        2. Negative Radiating Signs
        3. Normal SLR sitting and lying
        4. Normal ADL's

II. Independent Orthopedic Evaluation

Examiner:

J.A. Drews M. D.

– Report attached.

III. Recommendations

Mr. Doe is within normal range of motion for bilateral shoulders. Shoulder laxity is considered normal within test patterns for comparison of standard range of motions per AMA Guides. Gait patterns are normal in visual based comparisons.

Mr. Doe will benefit from a continued agility program for strength and speed.

Based on these examinations, we would clear him for continued participations in the national football league. Based on his seventeen year tenure, he may be more appropriate for spot plays.

IV. Predictions/Predictive modeling sample questions

To be queried by the EAIA Computing Apparatus a) If Ron Doe retired how would his impairments compare to other NFL offensive linemen?

b) Based on his multiple injury history, what is his expected NFL tenure?

c) What is the average career in years of a NFL offensive line?

d) What types of injuries are most common to offensive linemen?

e) What is the average injury claim cost of NFL offensive lineman?

f) What is the average injury settlement cost due to medical retirement and retirement at the end of a career?

g) What is normative data for aerobic fitness, speed tests, body composition, and strength for NFL offensive linemen?

H) What is normative data for NFL combine tests – broad jump, vertical jump, short shuttle, long shuttle, three-cone drill, and forty-yard dash for offensive linemen.

ORTHOPEDIC EVALUATION

| | |
|---|---|
| Player's Name: | Ron Doe |
| DOB: | 11-25-1968 |
| SSN: | 221-21-3331 |
| Date: | 12-15-2004 |

| | |
|---|---|
| Date of Examination | 12-11-2004 |
| Attending Physician: | J. A. Drews, M.D. |
| Identification: | The patient is a thirty-seven year old male offensive lineman who is being considering retirement from John Q Professional Football team unless cleared for participation. |
| Current Complaints: | The patient is a healthy, 305 lbs. male who injured His lumbar spine, L4/5 disc herniation, in November 2003. He currently reports he is free of acute injury and he has Completed regimen of physical therapy. He is Currently lifting and running under his own Supervision. |

Past Medical History:

3. He has had right anterior cruciate reconstruction performed in December 1991. He has no current symptoms of instability, swelling, or locking. He had bilateral shoulder partial rotator cuff repairs in 1995 and 1996. He has no current symptoms of instability, swelling, or limited use.

| | |
|---|---|
| <u>Medications:</u> | OTC – Aleve – as needed. |
| <u>Hospitalization:</u> | December 1991 – ACL reconstruction. |

Repair                            February 1995 – Rt. Shoulder RCT Partial

Repair                            February 1995 – Rt. Shoulder RCT Partial

Physical Examination:

| | | |
|---|---|---|
| Vital Signs: | Height: | 78 inches |
| | Weight: | 305 lbs. |
| | Blood Pressure: | 123/82 |
| | Pulse: | 80 bpm |
| | Respirations: | 20 pm |

Cervical Spine:      The patient's cervical spine is well aligned. He flexes to Point of touching his chin on his chest. He can extend fully. Rotation is present bilaterally to 80 degrees. Spurling's test is negative. No adenopathy is present. He had good cervical pulses.

Thoracic/Lumbar
Spine:      There is no evidence of scoliosis or lordosis. He has no limitation to flexion, extension, or lateral bending. He has no pain on motion. Straight Leg Raise (SLR) is negative. He has equal leg lengths. No atrophy of musculature in the lower extremity. MRI documented disk rupture L4-5 that is asymptomatic.

Neck:      He is not complaining of any radiating pain from his Neck. The range of motion (ROM) of the neck is normal. There is no occipital, paracervical, or trapezius tenderness to palpation. The reflexes, sensation, and muscle tone are normal.

Shoulders:
     Left:      He reports no pain with shoulder motion. He has no atrophy of shoulder muscles. He can forward flex and abduct his left shoulder to 180 degrees of motion and extend to 30 degrees. He can bring his left thumb to the level of T6 of his thoracic spine, suggesting excellent internal rotation and it is present at 40 degrees. He can externally rotate left shoulder to 95 degrees. He has

|  |  |
|---|---|
|  | negative apprehension sign. Impingement test is negative. He has no pain with rotation of shoulder. His strength testing of the rotator cuff muscles was normal. |
| Right: | He reports no pain with shoulder motion. He has no atrophy of shoulder muscles. He can forward flex and abduct his right shoulder to 180 degrees of motion and extend to 30 degrees. |
|  | He can bring his right thumb to the level of T6 of his thoracic spine, suggesting excellent internal rotation and it is present at 40 degrees. He can externally rotate right shoulder to 95 degrees. He has negative apprehension sign. Impingement test is negative. He has no pain with rotation of shoulder. His strength testing of the rotator cuff was five out of five. |
| Wrist/Hands: | He flexes and extends his fingers without pain or difficulty. His wrists flex and extend well. Grip strength is 160 lbs. on the right and 154 lbs. on the left. Pinch strength is 30 lbs. on the right and 29 lbs. on the left. This indicates no significant difference in grip strength in a right handed player. |
| Back: | He is not complaining of any radiating pain from his Back. The range of motion (ROM) of the back is normal. There is no tenderness to palpation. The reflexes, sensation, and muscle tone are normal. |
| Hips/Pelvis: | The hips and pelvis show that the pelvis is non-tender with palpation. His hips rotate fully and there is no indication flexion and extension. |
| Knees: | There is no effusion in either knee at the present time. |
| Left: | His left knee non-tender to palpation. His knee flexes to 130 degrees and extends to 0 degrees. He has no medial or lateral instability in 30 degrees of flexion. He has a negative flexion pinch test on both the medial and lateral menisci. His anterior cruciate shows an excellent end |

| | |
|---|---|
| | point. He has no pivot shifting. He has normal strength in his knee. |
| Right: | His right knee shows a well-healed anterior incision from the superior pole of the patella to the tibia tubercle along the medial aspect of his patella tendon. He has three portal incisions that are closed and well healed. He demonstrates 130 degrees flexion of the right knee and 0 degrees extension of his knee. He has no medial or lateral instability at 30 degrees of flexion. He has a solid end point with Lachman's and Anterior Drawer Tests. He has no patellofemoral crepitus or patella instability. McMurry's Test were negative. He has good quadriceps strength as well as hamstring strength. He has an essentially normal right knee examination. He has normal strength in his knee. |
| Ankles/Feet: | |
| Left: | The left foot is currently not bothering him. He reports a history of ankle sprains which were treated by medical staff at college. Standing alignment is normal with plantar flexion, dorsiflexion, inversion, and eversion ROMs within normal limits. |
| Right: | The right foot is currently not bothering him. He reports a history of ankle sprains which were treated by medical staff at college. Standing alignment is normal with plantar flexion, dorsiflexion, inversion, and eversion ROMs within normal limits. |
| Cardiac Examination: | The patient has a regular sinus rhythm of 80 bpm with no murmurs, clicks, or other abnormalities detected. |
| Pulmonary Examination: | The patient has clear lung fields bilaterally to auscultation and percussion. |
| Abdominal | |

Thus, the present invention is presently embodied as methods, systems, computer program products or computer readable mediums encoding computer programs for assesing athlete injuries.

It will be apparent to those skilled in the art that various modifications or variations may be made in the present invention without departing from the scope or spirit of the invention. Other embodiments of the present will be apparent to those skilled in the art from consideration of the specification and practice of the invention disclosed herein.

What is claimed is:

1. A computer-implemented method for assessing an injury to an athlete, the method comprising:
   receiving historical data associated with the athlete;
   receiving performance data from a functional assessment of the athlete wherein the functional assessment is designed based on at least one of the following: a sport of the athlete, a position of the athlete, and the injury of the athlete;
   calculating, by the computer, utilizing a data source, mined data associated with injuries similar to the injury being assessed, wherein the mined data is calculated by the data source utilizing a plurality of table structures within a database management system, the plurality of table structures comprising athlete, injury and treatment data, the mined data comprising at least one of the following:
   an average number of years, calculated by the data source, of future athletic performance by athletes with injuries similar to the injury being assessed, the average number of years comprising a number of years between an injury date and a career ending date associated with the athletes; and
   a percentage of athletes, calculated by the data source using a performance weighting value, having a predetermined number of a plurality years of future performance with injuries similar to the injury being assessed, wherein the injury being assessed comprises one of a plurality of different injuries incurred during an athletic career for the athlete;
   compiling the historical data and the performance data with the mined data for use in a creation of data relationships, statistical analysis, and data modeling employed in predicative analysis;
   querying, by the computer, the data source for the mined data;
   receiving, by the computer, the mined data as predictive data relevant to the injury; and
   analyzing at least one of the following: the historical data, the performance data, the mined data, and the predictive data to produce the predictive analysis associated with the athlete, wherein the analysis of the mined data produces a predictive analysis comprising an assessment of future athletic performance of the athlete for at least one year after the injury.

2. The method of claim 1, further comprising generating a report including the predictive analysis and recommendations based on the predictive analysis.

3. The method of claim 2, wherein generating a report including the predictive analysis and recommendations comprises calculating at least one of the following:
   impairment of the athlete at least in part due to the injury;
   predictive injury statistics based on percentiles and biostatistical measures;
   probability of the injury reoccurring; and
   marketability of the athlete based on the injury.

4. The method of claim 3, further comprising prior to querying a data source for mined data, generating the data source containing mined data associated with a plurality of injuries and athletes.

5. The method of claim 4, further comprising updating the data source with data associated with the predictive analysis.

6. The method of claim 5, wherein generating the data source comprises:
   receiving athlete injury data from at least one source;
   organizing the athlete injury data for accessibility to produce the mined data based on at least one of the following: sports associated with the athlete injury data, positions of athletes associated with the athlete injury data, physiology of the athletes associated with the athlete injury data, career status of the athletes associated with the athlete injury data, exposure of the athletes associated with the athlete injury data, and injuries associated with the athlete injury data; and
   storing the mined data in the data source.

7. The method of claim 1, further comprising receiving orthopedic data from an independent orthopedic assessment of the athlete; and
   analyzing the orthopedic data to produce the predictive analysis.

8. The method of claim 7, further comprising:
   receiving data associated with a brain typing evaluation of the athlete;
   receiving vocational data associated with a vocational assessment of the athlete; and generating a report for each one of the following:
      the independent orthopedic assessment;
      the functional assessment including generating the impairment;
      the predictive data relevant to the injury;
      the brain typing evaluation; and
      the vocational assessment.

9. The method of claim 1, wherein receiving historical data comprises receiving at least one of the following associated with the athlete:
   pre-existing medical conditions; and
   a current career status of the athlete;
   wherein the current career status comprises information associated with at least one of the following: a start of a career of the athlete, an injury during the career, and an end of the career.

10. The method of claim 1, wherein the predictive analysis is further used in association with at least one of the following:
   athlete contract negotiations;
   workmens compensation decisions;
   functional performance baselines due to a new injury;
   pre-existing injury assessments prior to athlete participation with a new team;
   career ending injury settlements;
   retirement settlements for injuries obtained during career;
   injury treatment recommendations; and
   expert opinions in court.

11. A computer program product comprising a computer-readable medium having control logic stored therein for causing a computer to assess an injury to an athlete, the control logic comprising computer-readable program code for causing the computer to:
   receive historical data associated with the athlete;
   receive performance data from a functional assessment of the athlete wherein the functional assessment is designed based on at least one of the following: a sport of the athlete, a position of the athlete, and the injury of the athlete;

calculate, utilizing a data source, mined data associated with injuries similar to the injury being assessed, wherein the mined data is calculated by the data source utilizing a plurality of table structures within a database management system, the plurality of table structures comprising athlete, injury and treatment data:

compile the historical data and the performance data with the mined data for use in a creation of data relationships, statistical analysis, and data modeling employed in a predicative analysis comprising an assessment of future athletic performance of the athlete for at least one year after the injury;

query the data source for the mined data;

receive the mined data as predictive data relevant to the injury and the athlete; and analyze at least one of the following: the historical data, the performance data, the mined data, and the predictive data to produce a predictive analysis associated with the athlete, wherein the analysis of the mined data produces the predictive analysis.

12. The computer program product of claim 11, further comprising computer-readable program code for causing the computer to generate a report including the predictive analysis and recommendations based on the predictive analysis.

13. The computer program product of claim 12, wherein the computer-readable program code for causing the computer to generate the report comprises computer-readable program code for causing the computer to calculate at least one of the following:

impairment of the athlete at least in part due to the injury;

predictive injury statistics based on percentiles and biostatistical measures;

probability of the injury reoccurring; and marketability of the athlete based on the injury.

14. The computer program product of claim 13, further comprising computer-readable program code for causing the computer to generate the data source containing mined data associated with a plurality of injuries and athletes prior to querying a data source for mined data.

15. The computer program product of claim 14, further comprising computer-readable program code for causing the computer to update the data source with data associated with the predictive analysis.

16. The computer program product of claim 15, wherein the computer-readable program code for causing the computer to generating the data source comprises computer-readable program code for causing the computer to:

receive athlete injury data from at least one source;

organize the athlete injury data for accessibility to produce the mined data based on at least one of the following: sports associated with the athlete injury data, positions of athletes associated with the athlete injury data, physiology of the athletes associated with the athlete injury data, career status of the athletes associated with the athlete injury data, exposure of the athletes associated with the athlete injury data, and injuries associated with the athlete injury data; and store the mined data in the data source.

17. The computer program product of claim 11, further comprising computer-readable program code for causing the computer to receive orthopedic data from an independent orthopedic assessment of the athlete; and analyze the orthopedic data to produce the predictive analysis.

18. A system for assessing an injury to an athlete, the system comprising:

a computer operative to:

receive historical data associated with the athlete;

receive personality characteristic data associated with the athlete;

receive performance data from a functional assessment of the athlete wherein the functional assessment is designed based on at least one of the following: a sport of the athlete, a position of the athlete, and the injury of the athlete;

calculate, utilizing a data source, mined data associated with injuries similar to the injury being assessed, wherein the mined data is calculated by the data source utilizing a plurality of table structures within a database management system, the plurality of table structures comprising athlete, injury and treatment data, the mined data comprising at least one of the following:

an average number of years, calculated by the data source, of future athletic performance by athletes with injuries similar to the injury being assessed, the average number of years comprising a number of years between an injury date and a career ending date associated with the athletes; and a percentage of athletes, calculated by the data source using a performance weighting value, having a predetermined number of a plurality years of future performance with injuries similar to the injury being assessed, wherein the performance weighting value comprises a numerical value gauging a role that a physical attribute of the athlete plays in effective performance of the position played by the athlete and wherein the injury being assessed comprises one of a plurality of different injuries incurred during an athletic career for the athlete;

compile the historical data the performance data, and the personality characteristic data with the mined data for use in a creation of data relationships, statistical analysis, and data modeling employed in predicative analysis comprising an assessment of future athletic performance of the athlete for at least one year after the injury;

query the data source for the mined data;

receive the mined data as predictive data relevant to the injury and the athlete; and analyze at least one of the following: the historical data, the performance data, the mined data, and the predictive data to produce the predictive analysis associated with the athlete, wherein the analysis of the mined data produces a predictive analysis comprising an assessment of future athletic performance of the athlete for at least one year after the injury; and a second computer operative to generate the data source containing mined data associated with a plurality of injuries and athletes prior to the computer querying the data source for mined data;

receive athlete injury data from at least the following sources:

an insurance company;

a guide to impairment;

a sports medicine institute;

sport league surveillance intelligence;

health care database;

professional sport league data bank; and a financial services system;

organize the athlete injury data for accessibility to produce the mined data based on at least one of the following: sports associated with the athlete injury data, positions of athletes associated with the athlete injury data, physiology of the athletes associated with the athlete injury data, career status of the athletes associated with the athlete injury data, exposure of the athletes associated with the athlete injury data, and injuries associated with the athlete injury data and store the mined data in the data source.

19. The system of claim 18, wherein the computer is further operative to calculate at least one of the following:
impairment of the athlete at least in part due to the injury;
predictive injury statistics based on percentiles and biostatistical measures;
probability of the injury reoccurring; and
marketability of the athlete based on the injury.

20. A business method for assessing an injury to an athlete which is implemented at least in part by a computer, the method comprising:
gathering medical history and information associated with the athlete to be assessed, the information comprising personality characteristics of the athlete used in a predictive analysis associated with the athlete;
designing and conducting a functional evaluation of the athlete;
conducting an independent orthopedic evaluation of the athlete by a certified a assessor;
calculating, by the computer, utilizing a data source, mined data associated with injuries similar to the injury being assessed, wherein the mined data is calculated by the data source utilizing a plurality of table structures within a database management system, the plurality of table structures comprising athlete, injury and treatment data;
compiling the history and information associated with the athlete, functional evaluation data of the athlete, and independent orthopedic evaluation of the athlete with the mined data for use in a creation of data relationships, statistical analysis, and data modeling employed in the predicative analysis;
querying, by the computer, the mined data to make predictions about the injury of the athlete;
providing the orthopedic and functional evaluation based on at least one of the following: a position, a sport, and the injury of the athlete; and
analyzing at least one of the following: the medical history and information, the functional evaluation, the orthopedic evaluation, the mined data based on the position, the sport, and the injury of the athlete therein making predictions regarding one of the following: the injury and the athlete.

* * * * *